(12) United States Patent
Solomon et al.

(10) Patent No.: US 9,750,879 B2
(45) Date of Patent: *Sep. 5, 2017

(54) BIOINJECTION DEVICE HAVING A TIP WITH A PLURALITY OF DIRECTIONAL DISPERSION APERTURES

(71) Applicants: Clifford T. Solomon, Hempstead, MD (US); Theodore C. Solomon, Hempstead, MD (US)

(72) Inventors: Clifford T. Solomon, Hempstead, MD (US); Theodore C. Solomon, Hempstead, MD (US)

( * ) Notice: Subject to any disclaimer, the term of this patent is extended or adjusted under 35 U.S.C. 154(b) by 158 days.

This patent is subject to a terminal disclaimer.

(21) Appl. No.: 14/060,484

(22) Filed: Oct. 22, 2013

(65) Prior Publication Data

US 2014/0058334 A1 Feb. 27, 2014

Related U.S. Application Data

(63) Continuation-in-part of application No. 13/708,772, filed on Dec. 7, 2012, now Pat. No. 8,968,235, which
(Continued)

(51) Int. Cl.
*A61B 17/88* (2006.01)
*A61M 37/00* (2006.01)
(Continued)

(52) U.S. Cl.
CPC ....... *A61M 5/2033* (2013.01); *A61B 17/7061* (2013.01); *A61B 17/8811* (2013.01);
(Continued)

(58) Field of Classification Search
CPC ............ A61M 5/2033; A61M 37/0069; A61M 5/3293; A61M 5/3134; A61M 2005/325;
(Continued)

(56) References Cited

U.S. PATENT DOCUMENTS 1,929,154 A * 10/1933 Sundock ............... A61M 13/00
604/201
3,774,607 A * 11/1973 Schmitz ............ A61M 37/0069
604/61
(Continued)

*Primary Examiner* — Bhisma Mehta
*Assistant Examiner* — Jenna Zhang
(74) *Attorney, Agent, or Firm* — Seed IP Law Group LLP

(57) ABSTRACT

The bioinjection device has a housing including a pistol grip and an elongated barrel. A trigger is pivotally mounted to the housing. An inner shaft having a distal end is slidable between a first position in which the distal end of the inner shaft is disposed in the barrel and a second position in which the distal end of the inner shaft extends past an opening in the end of the barrel. A tip containing a medicament is disposed about the opening of the elongated barrel. The tip includes at least one aperture for dispensing the medicament. One can inject the medicament from the tip into a bone fracture or degenerative bone tissue during surgery by actuating the trigger of the bioinjection device. A configurable tip may be employed to control the amount and direction of dispersion of such medicament.

19 Claims, 15 Drawing Sheets

Related U.S. Application Data is a continuation of application No. 12/901,208, filed on Oct. 8, 2010, now Pat. No. 8,328,753, which is a continuation of application No. 12/458,779, filed on Jul. 22, 2009, now Pat. No. 7,824,539.

(60) Provisional application No. 61/129,849, filed on Jul. 24, 2008.

(51) Int. Cl.
| | | |
|---|---|---|
| *A61M 5/20* | (2006.01) | |
| *A61N 5/10* | (2006.01) | |
| *A61B 17/70* | (2006.01) | |
| *A61B 17/34* | (2006.01) | |

(52) U.S. Cl.
CPC ....... *A61M 37/0069* (2013.01); *A61N 5/1007* (2013.01); *A61B 17/3472* (2013.01); *A61M 2210/02* (2013.01)

(58) Field of Classification Search
CPC ... A61M 2005/3132; A61M 2005/3118; A61B 17/3468; A61B 5/1007; A61B 17/7061; A61B 17/8811
See application file for complete search history.

(56) References Cited

U.S. PATENT DOCUMENTS

| | | | |
|---|---|---|---|
| D261,425 S | 10/1981 | Bruhn | |
| 4,338,925 A | 7/1982 | Miller | |
| 4,405,249 A | 9/1983 | Scales | |
| 4,518,384 A | 5/1985 | Tarello et al. | |
| 4,546,767 A | 10/1985 | Smith | |
| 4,762,515 A * | 8/1988 | Grimm | A61M 37/0069 604/61 |
| 4,787,384 A * | 11/1988 | Campbell | A61M 37/0069 604/60 |
| 4,815,454 A | 3/1989 | Dozier, Jr. | |
| 5,052,243 A | 10/1991 | Tepic | |
| 5,135,493 A * | 8/1992 | Peschke | A61M 37/0069 604/57 |
| 5,147,295 A * | 9/1992 | Stewart | A61M 37/0069 604/61 |
| 5,281,197 A * | 1/1994 | Arias | A61M 37/0069 604/209 |
| 5,312,333 A | 5/1994 | Churinetz et al. | |
| 5,431,654 A | 7/1995 | Nic | |
| 5,522,797 A * | 6/1996 | Grimm | A61D 7/00 604/61 |
| 6,132,364 A * | 10/2000 | Rottenberg | A61M 1/1037 600/16 |
| 6,309,395 B1 | 10/2001 | Smith et al. | |
| 6,428,463 B1 * | 8/2002 | Ravins | A61M 37/0069 600/7 |
| 6,439,439 B1 | 8/2002 | Rickard et al. | |
| 8,328,753 B2 | 12/2012 | Solomon et al. | |
| 8,968,235 B2 * | 3/2015 | Solomon et al. | 604/62 |
| 2002/0010472 A1* | 1/2002 | Kuslich | A61B 17/7095 606/93 |
| 2004/0019355 A1 | 1/2004 | Mehdizadeh | |
| 2006/0015067 A1 | 1/2006 | Bates | |
| 2007/0100449 A1 | 5/2007 | O'Neil et al. | |
| 2007/0255287 A1 | 11/2007 | Rabiner | |
| 2008/0009792 A1* | 1/2008 | Henniges | A61B 17/3472 604/98.01 |
| 2011/0034885 A1* | 2/2011 | Biyani | A61B 17/8811 604/272 |

* cited by examiner

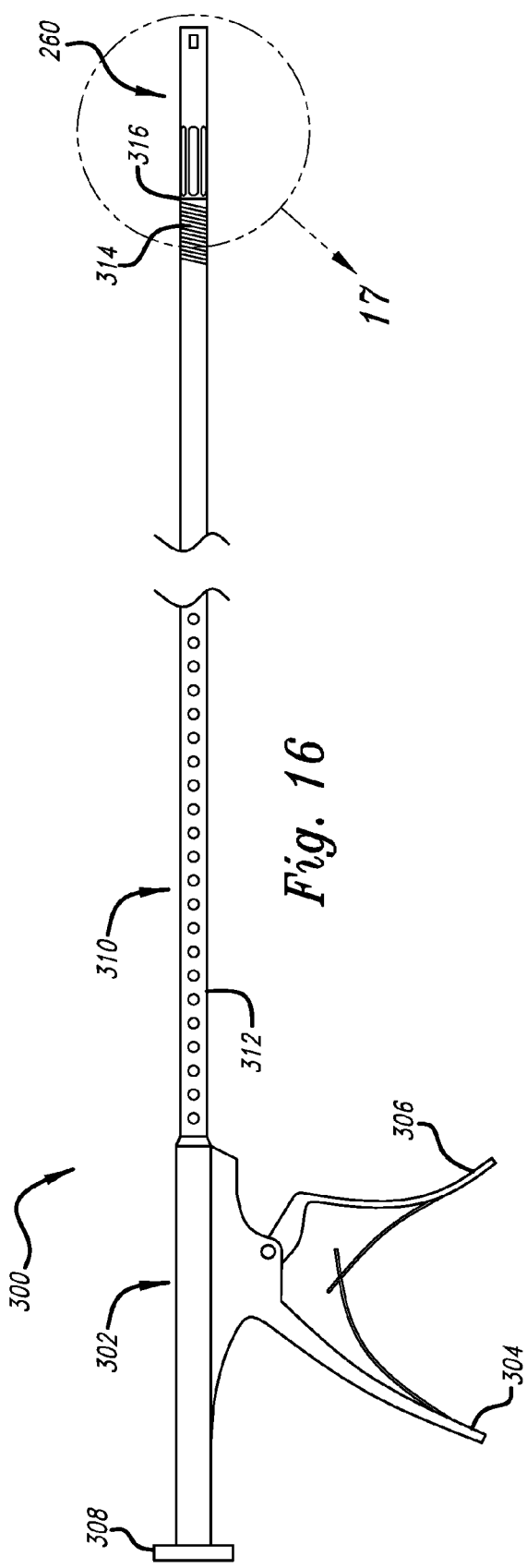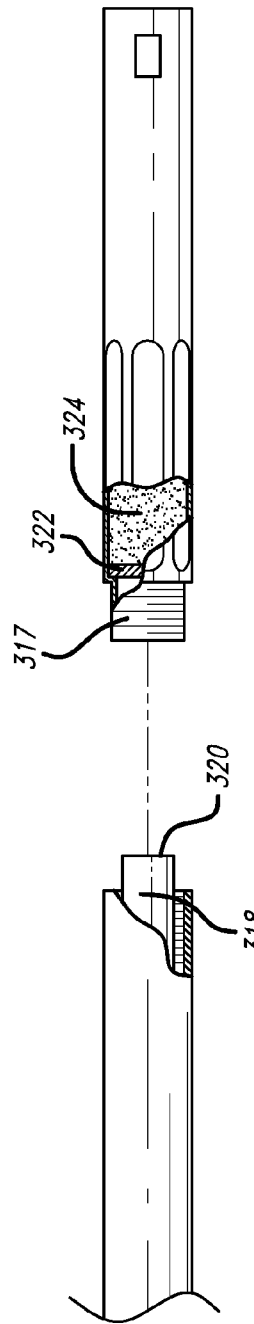

BIOINJECTION DEVICE HAVING A TIP WITH A PLURALITY OF DIRECTIONAL DISPERSION APERTURES

CROSS-REFERENCE TO RELATED APPLICATIONS

This application is a continuation-in-part of U.S. patent application Ser. No. 13/708,772, filed Dec. 7, 2012 entitled BIOINJECTION DEVICE, which is a continuation of U.S. patent application Ser. No. 12/901,208, filed Oct. 8, 2010, now U.S. Pat. No. 8,328,753, entitled BIOINJECTION DEVICE, which is a continuation of U.S. patent application Ser. No. 12/458,779, filed Jul. 22, 2009, now U.S. Pat. No. 7,824,359, issued Nov. 2, 2010, entitled BIOINJECTION DEVICE, which claims the benefit of U.S. Provisional Patent Application Ser. No. 61/129,849, filed Jul. 24, 2008, the contents of which are incorporated herein by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

The present invention relates to devices for the delivery of pharmaceuticals, and particularly to a bioinjection device for delivering bone morphogenic protein, antibiotics, etc., directly to the site of a bone fracture, degenerative bone tissue or cartilage, etc., during the course of surgery in the form of a bioabsorbable matrix enclosed within a membrane cartridge.

DESCRIPTION OF THE RELATED ART

Bone is a living tissue and plays a structural role in the body. Disease and damage, however, is often difficult to treat in bones, due to their positioning within the soft tissues of the body. Bone consists of repeating Haversian systems (concentric layers of lamellae deposited around a central canal containing blood vessels and nerves). The central canal is also known as the medullary cavity and is filled with bone marrow. Within the shaft of a long bone, many of these Haversian systems are bundled together in parallel, forming a type of bone called compact bone, which is optimized to handle compressive and bending forces. In some bones, such as the metacarpals, for example, the bones themselves are hollow and contain little, if any, marrow. Near the ends of the bones, where the stresses become more complex, the Haversian systems splay out and branch to form a meshwork of cancellous or spongy bone. Compact bone and cancellous bone differ in density, or how tightly the tissue is packed together.

Genetic or developmental irregularities, trauma, chronic stress, tumors, and disease can result in pathologies of bones. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures becomes important. Severe fractures, such as those that are open, multiple, or to the hip or back, are typically treated in a hospital. Surgery may be necessary when a fracture is open, severe, or has resulted in severe injury to the surrounding tissues. Severe fractures may require internal devices, such as screws, rods, or plates, to hold the bone in place or replace lost bone during the healing process.

In order to repair severe fractures, bone cement and the like is often applied within the fracture. However, other healing agents, such as antibiotics or bone morphogenic proteins, often need to be applied prior to cementing or performance of other operations on the bone. Due to the awkward positioning of bone fractures within other tissue, it is often quite difficult to properly apply medicaments and the like within the bone, particularly without damaging the tissue surrounding the bone. Thus, a bioinjection solving the aforementioned problems is desired.

SUMMARY

The bioinjection device is directed towards a device for injecting or implanting a membrane-encased cartridge of pharmaceuticals and/or biologics, bone grafts, radioactive seeds and the like, in a bioabsorbable matrix or carrier directly into the site of a bone fracture, degenerative bone tissue or cartilage, or the like in the course of surgery. The cartridge may contain bone morphogenic protein, antibiotics, bone, bone substitute or the like.

The device includes a housing having an upper portion and a lower gripping portion. The lower gripping portion may be rotatable with respect to the upper portion and includes a handle member and a trigger member. The trigger member is pivotally secured to the handle member. Further, the upper portion of the housing has an open interior region formed therein.

A shaft is slidably mounted within the open interior region of the upper portion of the housing. The shaft has opposed forward and rear ends and is elongated along a longitudinal axis. Further, the shaft has a channel formed therethrough, also extending along the longitudinal axis from the forward end to the rear end.

At least one lever arm is pivotally mounted within the housing, with the at least one lever arm having opposed first and second ends. The first end of the lever arm is attached to the rear end of the shaft, and the second end is attached to the trigger member so that rotation of the trigger member with respect to the handle member drives sliding translation of the shaft with respect to the upper portion of the housing.

A needle is slidable within the channel formed through the shaft, the needle having opposed front and rear ends. The front end of the needle terminates in a relatively sharp point. The rear end thereof is attached to the at least one lever arm so that rotation of the trigger member with respect to the handle member drives forward sliding translation of the needle with respect to the upper portion of the housing and the shaft. Preferably, the at least one lever arm includes a pair of lever arms, including a first lever arm driving movement of the shaft and a second lever arm driving movement of the needle.

A retaining member has opposed front and rear ends. The front end is open and the rear end is attached to a forward portion of the upper portion of the housing. An opening is formed through the rear end of the retaining member and the forward portion of the upper portion so that the forward end of the shaft and the front end of the needle selectively and slidably project therethrough into an open interior region of the retaining member. The retaining member is preferably releasably attached to the forward portion of the upper portion of the housing.

A cartridge is releasably received within the open interior region of the retaining member. The cartridge includes an outer shell membrane and a medicament contained within the outer shell. The forward end of the shaft contacts the membrane so that actuation of the trigger member causes the shaft and the needle to slide forward, with the shaft pushing the cartridge out of the retaining member for deployment thereof into the bone fracture. As the shaft pushes the implant out of the retaining member, the needle pierces the outer shell membrane to release the medicament into the fracture or degenerative tissue.

In another embodiment, a bioinjection device may include a housing having a handle member and an elongated barrel connected to the handle member. The elongated barrel includes a channel and a distal end defining an opening. A trigger is pivotally mounted on the housing of the device. Also, an inner shaft having an end portion (blunt, rounded, or pointed end) is received within the channel of the elongated barrel. The inner shaft is slidable along the channel of the elongated barrel between a first position in which the end portion of the inner shaft is retracted within the elongated barrel and a second position in which the end portion of the inner shaft extends past the opening at the distal end of the elongated barrel. The bioinjection device of this embodiment also includes a tip containing a medicament disposed about the opening at the distal end of the elongated barrel. The tip may include one aperture or opening for dispensing the medicament, and the tip may include a plurality of apertures or openings. A spring-loaded actuation mechanism couples the trigger with the inner shaft to force medicament contained in the tip through the aperture of the tip into a body tissue when the trigger is actuated.

In one embodiment, the bioinjection device may include a directional control member that is operative to selectively control the amount of dispersion of medicament from one or more of the plurality of tip apertures. The directional control member may be rotatable to close at least one aperture while leaving at least one aperture in an open position for dispensing the medicament. Also, the directional control member may be used to control the location or angle of dispersion of the medicament from the tip into the body tissue.

It has been contemplated that the tip of the bioinjection device includes apertures that are located equal-distant about the circumference of the tip. The positioning of the apertures may be located anywhere along the circumference of the tip or at the distal end of the tip. Further, the tip apertures may have a diameter of about 10 millimeters to about 17 millimeters. The tip apertures may also be about 5 millimeters in length. Also, tip apertures may vary in size, one from the other. The shape of the tip apertures may also vary, one from the other. In other embodiments, the tip apertures are all of the same shape and size.

The tip may be removably attached to the bioinjection device, and therefore, one tip may be replaced with a different tip having different apertures, structures, or medicament. Further, the medicament can be prepared to a desired specification during a procedure and placed within a tip to be used with the bioinjection device. The medicament may be comprised of autograft, allograft, or BMP.

In yet another embodiment, the tip of the bioinjection device may have apertures that are in an initially sealed state. In use, one of more of the apertures can subsequently be opened by a user of the bioinjection device to control the direction of dispersion of the medicament through one or more apertures located on the tip. More specifically, the apertures may be selectively opened, perforated, or removed to control the direction or angle of medicament dispersion from the tip of the bioinjection device. The apertures may be sealed using foil, plastic, silicon, polymers, acrylics, or metal strips.

These and other features of the present invention will become readily apparent upon further review of the following specification and drawings.

BRIEF DESCRIPTION OF THE DRAWINGS

FIG. 16 is a side view of an alternative embodiment of a bioinjection device; and FIG. 17 is an enlarged view of the distal end of the bioinjection device shown in FIG. 16.

Similar reference characters denote corresponding features consistently throughout the attached drawings.

DETAILED DESCRIPTION

Figure 1:
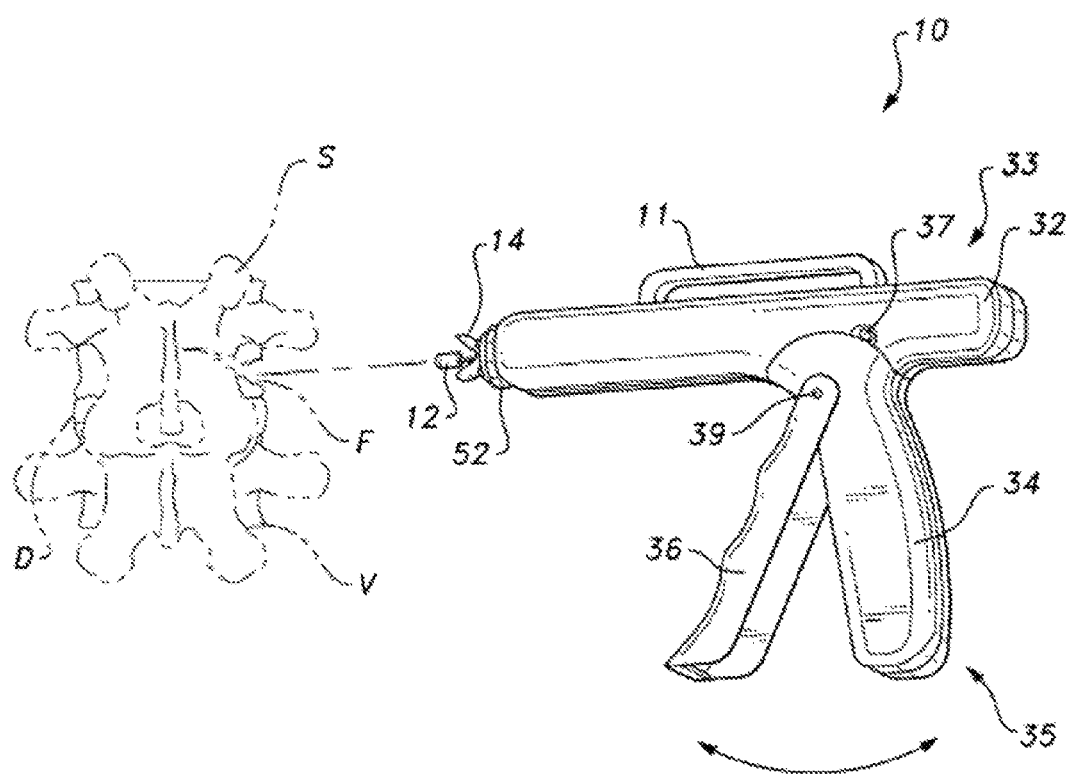
FIG. 1 is an environmental, perspective view of a bioinjection device.

The present invention relates to a bioinjection device 10. As shown in FIG. 1, device 10 is used to place a cartridge 12 into a fracture, degenerative tissue, or the like of a spinal segment S. The cartridge 12 contains a medicament (bone morphologic protein, antibiotics, or the like disposed in a bioabsorbable matrix or carrier) for the healing of the spinal segment S. It should be understood that spinal segment S, having vertebral bodies V, disc D and facet joint F, of FIG. 1 is shown for exemplary purposes only and is not intended to limit the type of bone or fracture that the cartridge 12 and device 10 may be used to treat.

Figure 2:
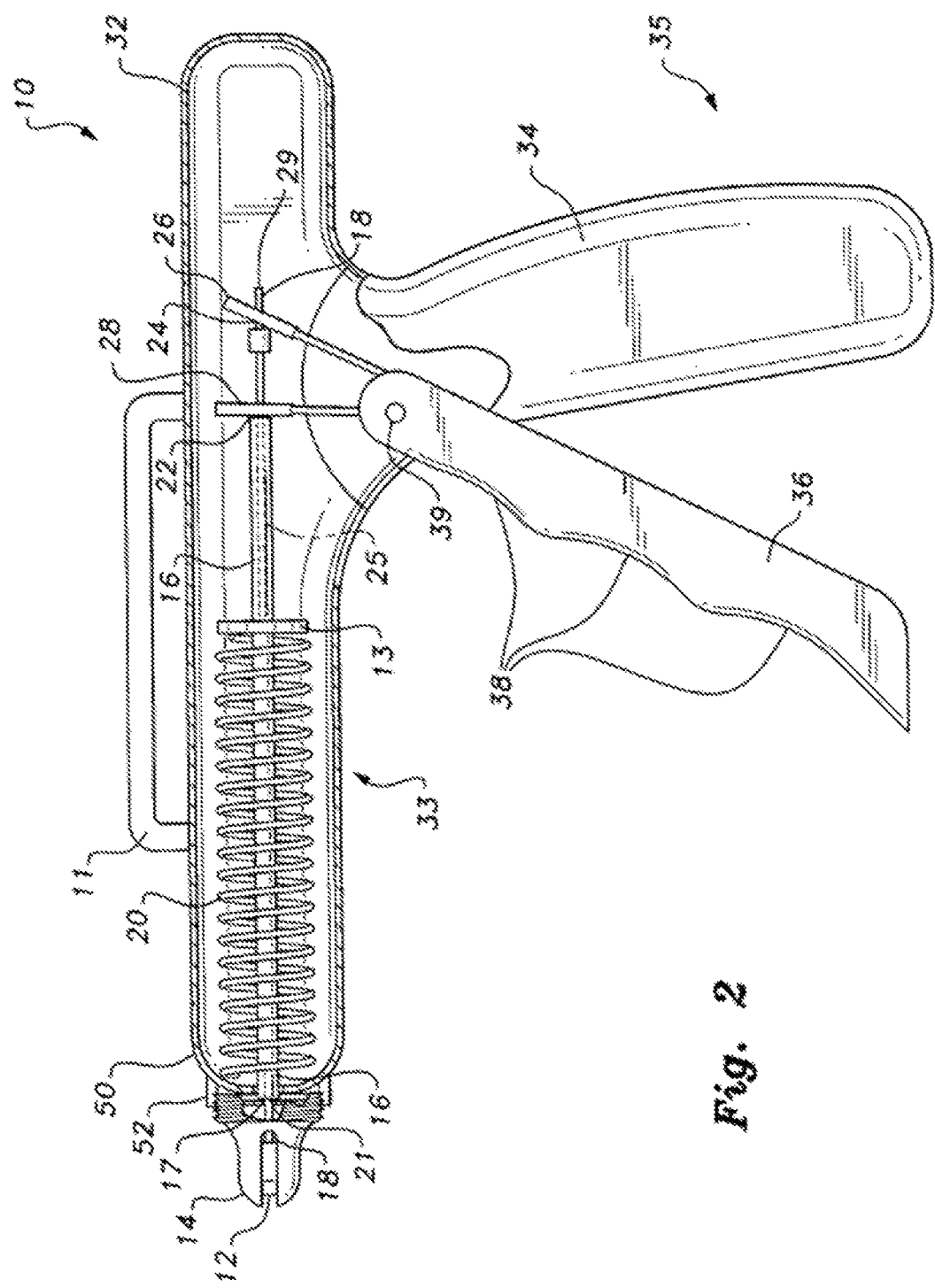
FIG. 2 is a side view of the bioinjection device, broken away and partially in section to show details thereof.

As best shown in FIGS. 1 and 2, the device 10 includes a housing 32 having a barrel-shaped upper portion 33 and a lower gripping portion 35. The lower gripping portion 35 may be rotatable with respect to the upper portion 33 and includes a pistol grip handle member 34 and a trigger member 36. The trigger member 36 is pivotally secured to the handle member 34 by a pivot pin 39 or the like. Trigger member 36 preferably has a plurality of finger receiving grooves or recesses 38 formed therein, as shown in FIG. 2, allowing for optimal gripping and actuation by the surgeon. Further, an upper gripping handle 11 may be mounted on an upper surface of housing 32, allowing the surgeon to better grip and secure tool 10 during the surgical operation.

As noted above, the lower portion 35, including both handle member 34 and trigger member 36, may be rotatable about pivot 37, allowing the lower gripping portion 35 to be rotated if necessary, depending upon the nature of the particular operation. The lower portion 35 may further be selectively locked in place with respect to the upper portion 33. Further, as shown in FIG. 2, the barrel-shaped upper portion 33 of housing 32 has an open interior region formed therein.

As shown in FIG. 2, a shaft 16 is slidably mounted within the open interior region of the upper portion 33 of the housing 32. The shaft has opposed forward and rear ends 21, 22, respectively, and is elongated along a longitudinal axis, as shown. Further, the shaft 16 has a longitudinally extending channel 25 formed therethrough, extending from the forward end 21 to the rear end 22. Shaft 16 is preferably resiliently or spring-biased with respect to housing 32. In the preferred embodiment, a stop 13, such as a disc, is mounted to a central portion of shaft 16, as shown in FIG. 2, with a spring 20 or other resilient element being biased between the stop 13 and the inner wall of forward portion 50 of housing 32.

At least one lever arm is pivotally mounted within housing 32 for the actuation of shaft 16. Preferably, the at least one lever arm includes a pair of lever arms with a first lever arm 28 driving movement of the shaft 16, and a second lever arm 26 driving movement of needle 18, as will be described in greater detail below. First lever arm 28 has opposed first and second ends, with the first end of first lever arm 28 being secured to the rear end 22 of shaft 16, and the second end being secured to the trigger member 36 so that rotation of the trigger member 36 with respect to the handle member 34 drives sliding translation of the shaft 16 with respect to the upper portion 33 of the housing 32.

Figure 4:
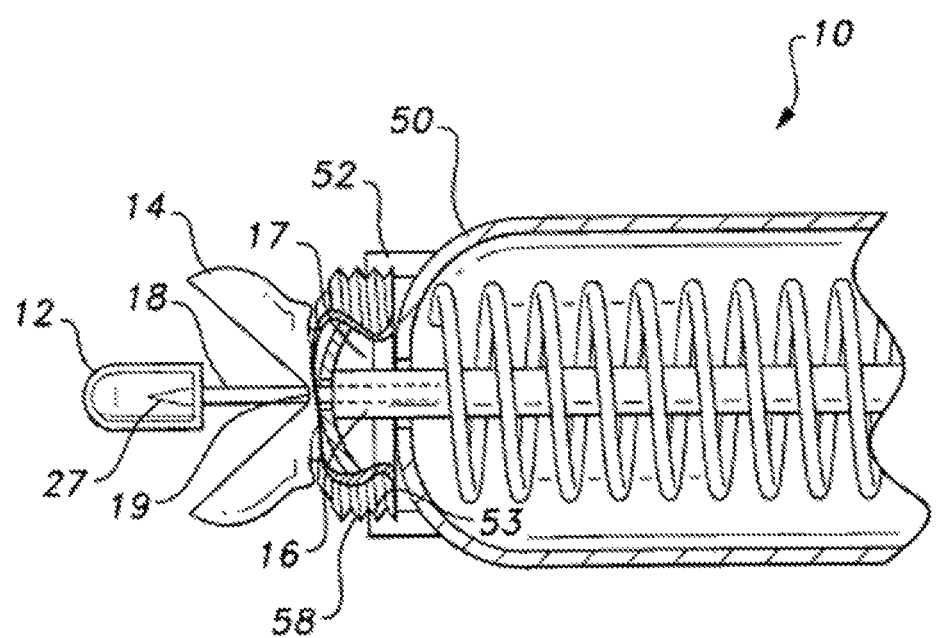
FIG. 4 is a partial side view in section of the bioinjection device, showing a cartridge extended from the device for injection or implantation.

Needle 18 is slidably received within the channel 25 formed through the shaft 16, with the needle 18 having opposed front and rear ends 27, 29, respectively (the front end or tip 27 of needle 18 is best shown in FIG. 4). The front end 27 of needle 18 is preferably formed as a relatively sharp point. The rear end 29 of needle 18 is secured at 24 to the second lever arm 26 so that rotation of trigger member 36 with respect to the handle member 34 drives forward sliding translation of the needle 18 with respect to the upper portion 33 of the housing 32 and also with respect to the shaft 16; i.e., actuation of trigger member 36 causes forward sliding of shaft 16 within the housing 32 and also forward sliding of needle 18 within the shaft 16.

A retaining member 14 is further provided, with the retaining member having opposed front and rear ends. As shown, retaining member 14 preferably forms a pair of gripping jaws for releasably holding implant 12. The front end thereof is open and the rear end thereof is secured to mounting member 52, which is fixed to a forward portion 50 of the upper portion 33 of the housing 32. The rear portion of retaining member 14 is preferably releasably attached to the mounting member 52 through use of any suitable releasable fastener. The rear portion may have threads 58 formed thereon, as best shown in FIG. 4, for reception by a threaded recess 53 formed in mounting member 52.

Further, an opening 19 is formed through the rear end of the retaining member 14, and a passage 17 is formed through the forward portion 50 of housing 32 so that the forward end 21 of shaft 16 and the front end 27 of the needle 18 selectively and slidably project therethrough into an open interior region of the retaining member 14.

Figure 3:
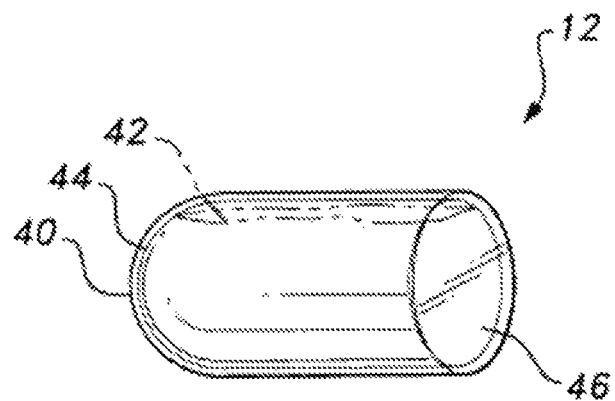
FIG. 3 is a perspective view of a membranous cartridge for use with a bioinjection device.

Cartridge 12 is releasably received within the open interior region of the retaining member 14. As best shown in FIG. 3, the cartridge 12 includes an outer shell membrane 40 and a medicament 42 contained within the outer shell 40. The medicament 42 may be a bone morphogenic protein, bone void filler, an antibiotic, or any other desired medicament for the healing of the bone, and may be disposed in a bioabsorbable matrix or carrier. The outer shell may be formed from hydroxyapatite calcium phosphate, or any other biodegradable material that will dissolve and/or fuse within the bone. Preferably, the rear end 46 of shell 40 is formed as a relatively thin membrane that can be pierced by tip 27 of needle 18. A further thin membrane 44 may be formed between the outer shell 40 and the medicament 42.

In use, the cartridge 12 is positioned within retaining member 14, as shown in FIG. 2, with the forward end 21 of shaft 16 contacting the rear surface 46 of the bone implant 12. Actuation of trigger member 36 causes the shaft 16 and the needle 18 to slide forward. Retaining member 14 is preferably formed from a flexible material, such as rubber, plastic or the like, so that forward movement of shaft 16 pushes the cartridge 12 out of the open front end of the retaining member 14 for deployment thereof into the bone fracture or other damaged or diseased area. As the shaft 16 pushes the cartridge 12 out of the retaining member 14, the tip 27 of needle 18 pierces the thin membrane 46 to release the medicament 42 into the fracture. The surgeon lodges the pierced cartridge 12 within fracture F or the degenerative bone tissue.

Figure 9:
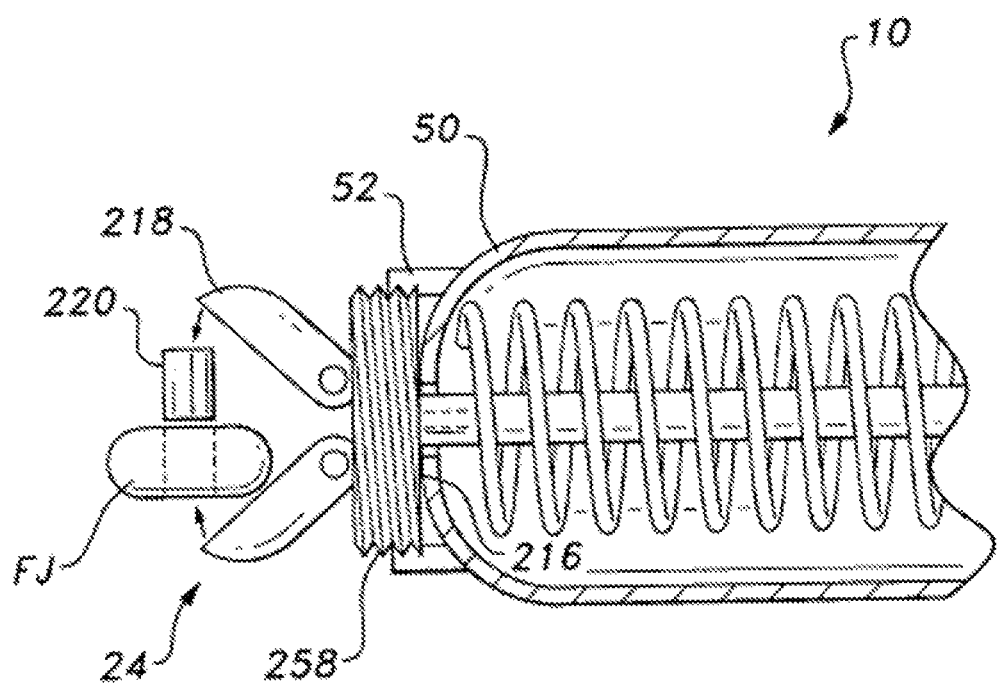
FIG. 9 is a side view of an alternative embodiment of the head of the bioinjection device.

In FIG. 9, retaining member or head 14 of FIG. 4 has been replaced by an alternative head 214, having a rear portion 216 with threads 258, similar to threaded connection 58 of FIG. 4. A pair of spring-biased jaws 218 are mounted to the rear portion 216, with one or both of the jaws 218 being adapted for releasably gripping a bone dowel 220 or the like for insertion into a facet joint FJ. In the embodiments of FIGS. 2 and 9, the heads 14, 214 and the shaft have relatively small sizes, allowing for placement within the facet joint, as noted above. However, it should be understood that the head and/or shaft might have any suitable size, dependent upon the site for placement of the cartridge. As will be described in detail below, a longer shaft and head may be necessary for injection of cartridges within a larger or longer bone, such as a tibia, and the shaft and head may be appropriately sized dependent upon the intended injection site.

Figure 6A:
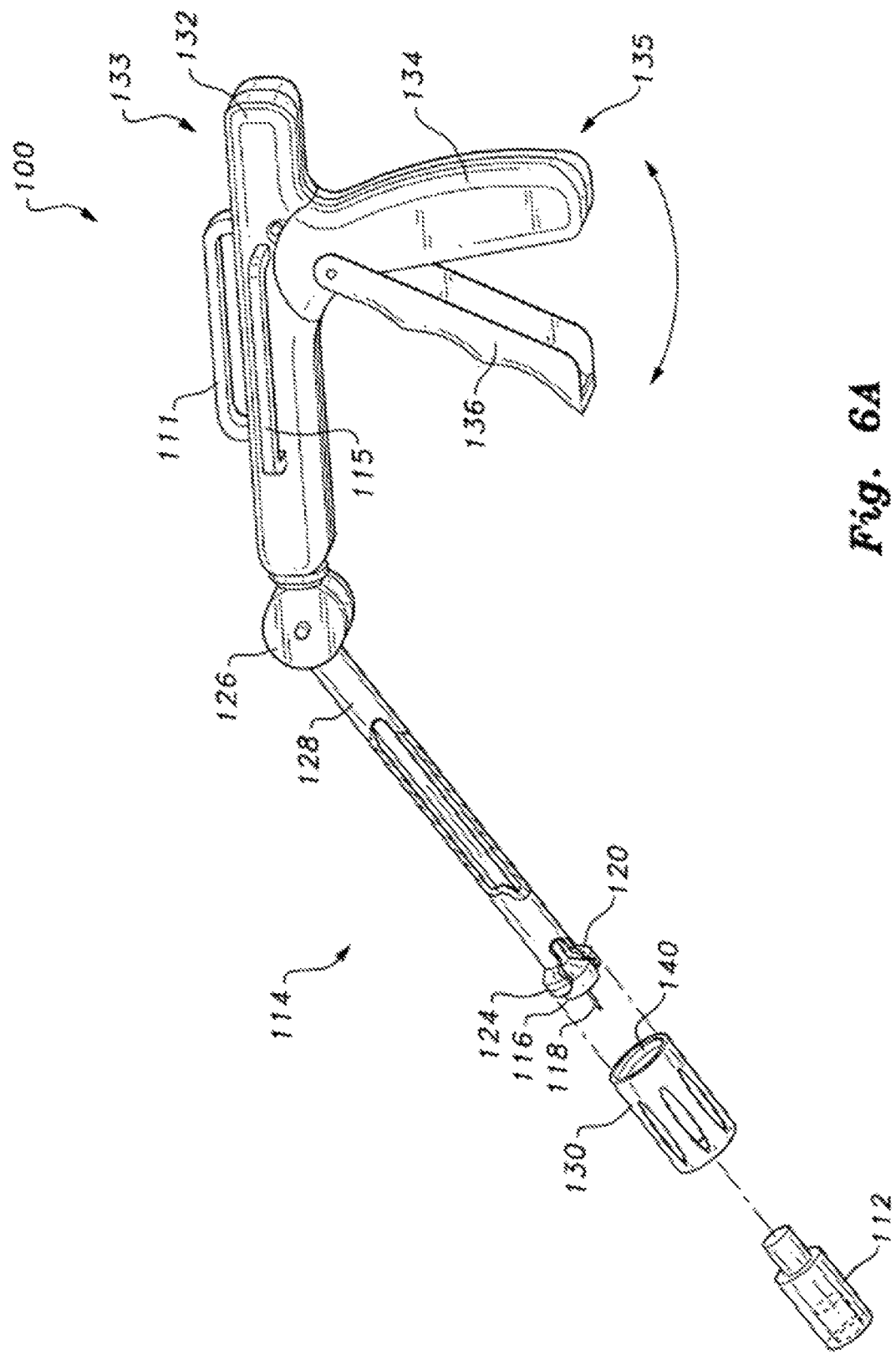
FIG. 6A is a perspective view of an alternative embodiment of the bioinjection device.

FIG. 6A illustrates an alternative embodiment of the bioinjection device. Bioinjection device 100 includes a housing 132 having upper and lower portions 133, 135, similar to that of the embodiment of FIGS. 1-4. Similarly, the lower portion 135 includes a handle member 134 and a trigger member 136, and the upper portion 133 has a handle 111 mounted thereon. Side handles 115 may also be mounted to upper portion 133, as shown, offering the surgeon a variety of gripping surfaces for differing angles of insertion during an operation. In the embodiment of FIG. 6A, an elongated tube 114 is mounted to the front end of barrel-shaped upper portion 133, allowing for the implanting of bone implants where immediate proximity of the surgeon's hands is not possible, such as in the implantation of implants 112 within channel C formed in tibia T of FIG. 8.

The elongated tube 114 includes an adjustable portion 126, allowing for angular adjustment of the tube 114 adjacent the front end of the upper portion 133 of housing 132. Adjustable portion may be a rotating and selectively locking disc member, as shown, or may be any other suitable angular adjustment device. A central region 128, preferably being solid and relatively non-flexible, is joined to the flexible portions 126 at one end thereof, and a head 120 is disposed at the other end of tube 114. Head 120 has an open outer end with external threads 124 formed therearound.

The retaining jaws 14 of the embodiment of FIGS. 1-5 are replaced in FIG. 6A by a cylindrical retaining member 130 having opposed open ends. Retaining member 130 is formed from a resilient, flexible material, similar to that described above with regard to jaws 14. Internal threads 140 are formed in one end of the retaining member 130 for releasable attachment to the head 120 via engagement with threads 124. It should be understood that retaining member 130 may be releasably secured to head 120 through any suitable releasable fastener.

An implant 112 is received within retaining member 130 for selective dispensing thereof. Similar to that described above with regard to the embodiment of FIGS. 1-5, an inner shaft 116, similar to shaft 16, extends through tube 114 and is shown in FIG. 6A slightly projecting from head 120. Shaft 116 preferably has a plunger-type shape, as shown, with a relatively wide outer face for pushing the wider implant 112. A needle 118, similar to needle 18, is housed within shaft 116. The alternative embodiment of FIG. 6B is substantially similar to that shown in FIG. 6A, but shaft 116 terminates in a covering head 117, which covers and surrounds the needle 118 and prevents the needle 118 from becoming caught in the implant 112. In operation, the user actuates trigger 136 to slide the shaft 116 and needle 118 forward so that the shaft 116 pushes the implant 112 out of retaining member 130 and needle 118 pierces the implant 112, as described above. When retaining member 130 is fixed to head 120, the head of plunger 116 will project out from retaining member 130 (when the trigger is compressed) by approximately one or two mm.

Figure 7:
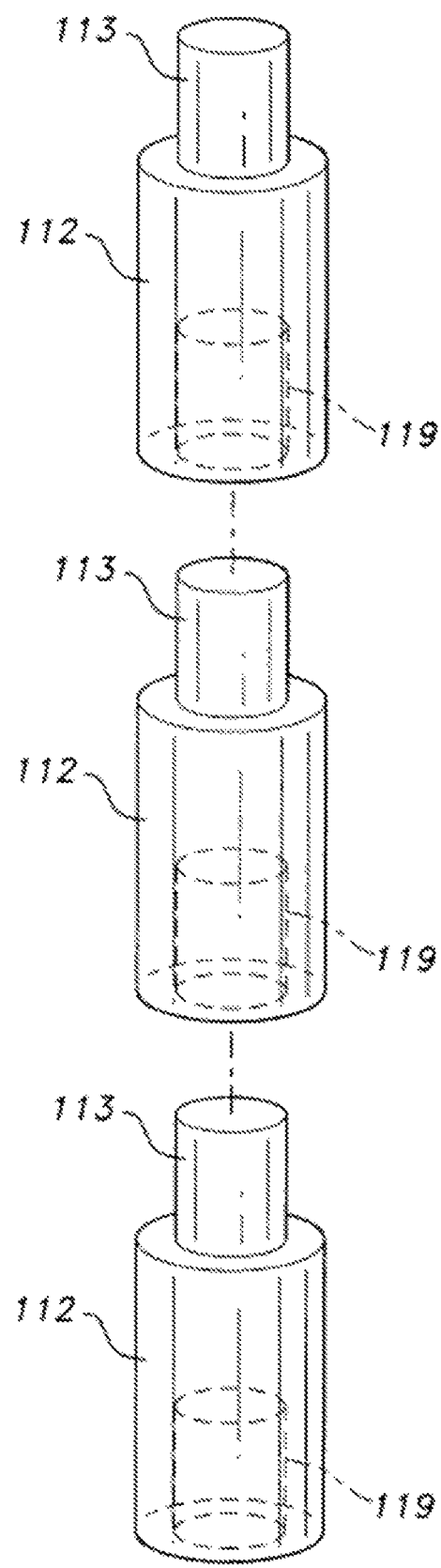
FIG. 7 is an exploded view of a plurality of alternative bone implants for use with the bioinjection device.

Implant 112 is preferably formed from materials similar to those described above with reference to implant 12. However, as best shown in FIG. 7, implant 112 preferably includes an upper projecting member 113 and a lower recess 119. As shown in FIG. 7, multiple implants 112 may be stacked through insertion of an upper projecting member 113 into a lower recess 119 of an adjacent implant.

Figure 5:
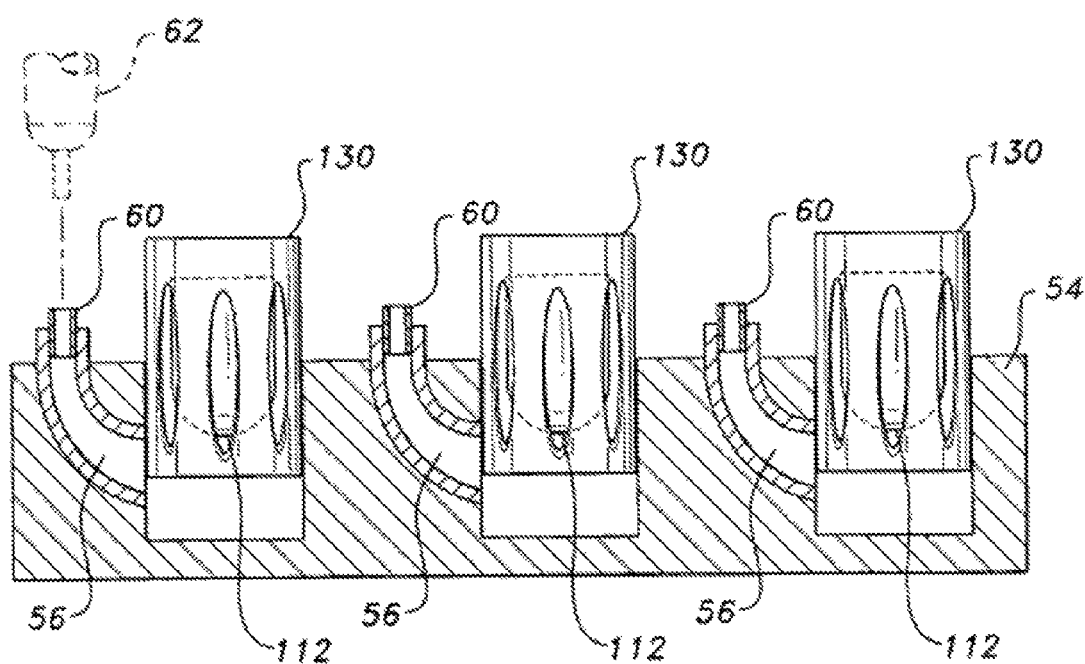
FIG. 5 is a side view of a plurality of removable and fillable heads of a bioinjection device according to the present invention.
Figure 6B:
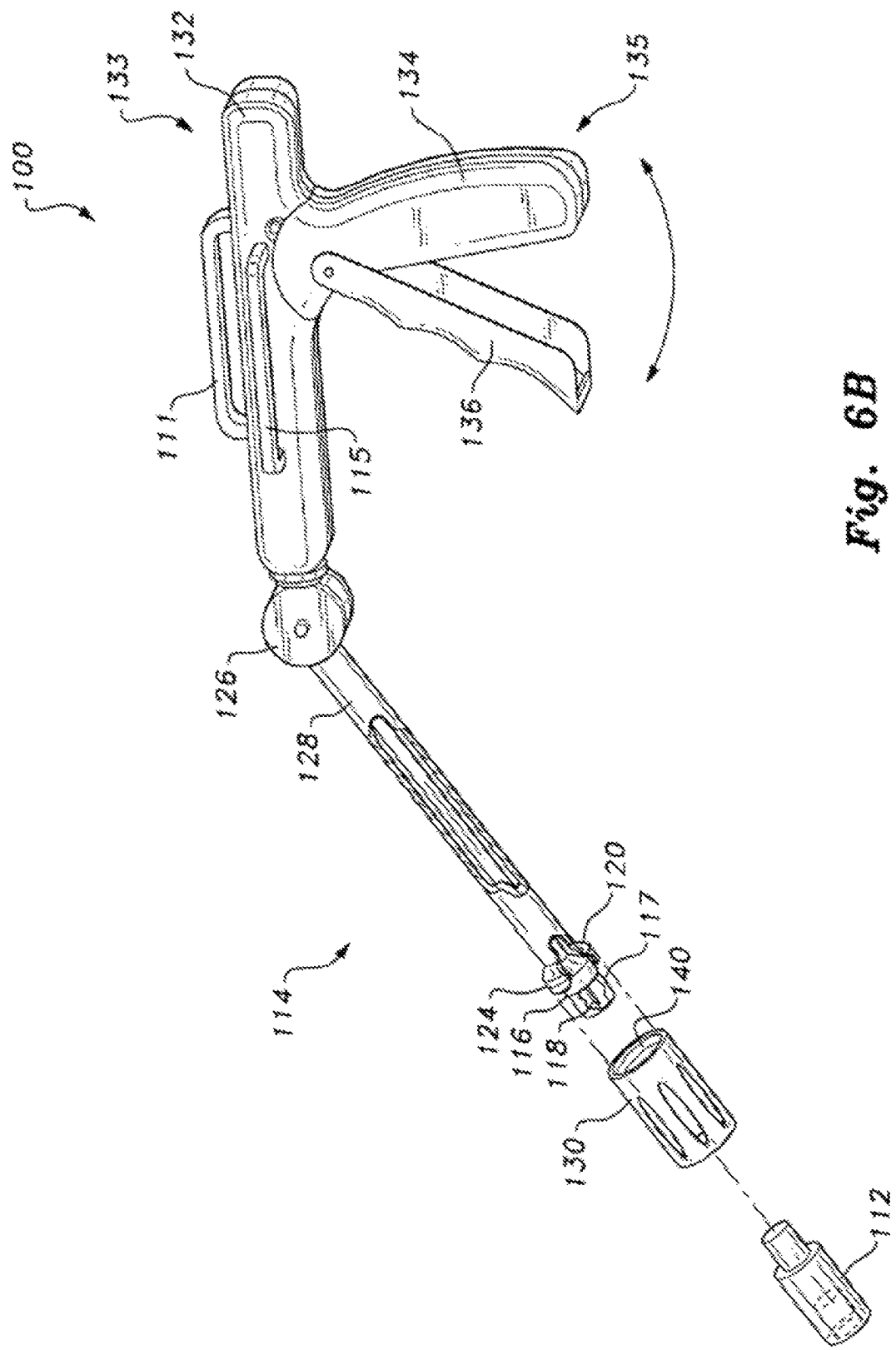
FIG. 6B is a perspective view of another alternative embodiment of the bioinjection device.

As shown in FIG. 5, the removable retaining members 130 may be stored and filled within a tray 54. In order to allow for quick insertion and replacement of cartridges 112, cartridges 112 may be positioned within retaining members 130, as shown. Tray 54 preferably includes a plurality of channels 56 for filling of cartridges 112 within the stored retaining members 130. A syringe 62 or other supply of medicament may be applied to ports 60, which cover and seal channels 56, allowing the medicament to be transferred to the cartridges 112. Communication with, and filling of, cartridges 112 may be accomplished through any suitable fluid transfer mechanism.

Figure 8:
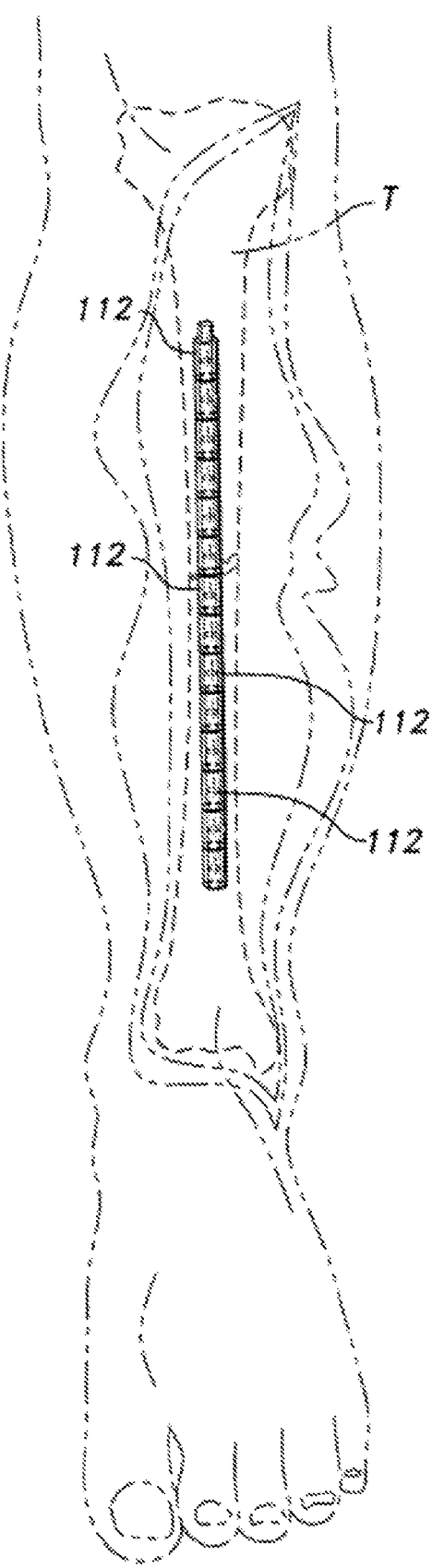
FIG. 8 is a front view of a human leg broken away to show the bone implants of FIG. 7 inserted within a channel formed within a bone.

FIG. 8 illustrates this stacked implantation within a channel C formed within an exemplary tibia T. Such channels C are often formed from the talus to the knee during the implantation of rods and the like in tibial reconstruction. The device 100 of FIG. 6 allows for easy insertion of multiple implants 112 within channel C after removal of such a rod.

Figure 10:
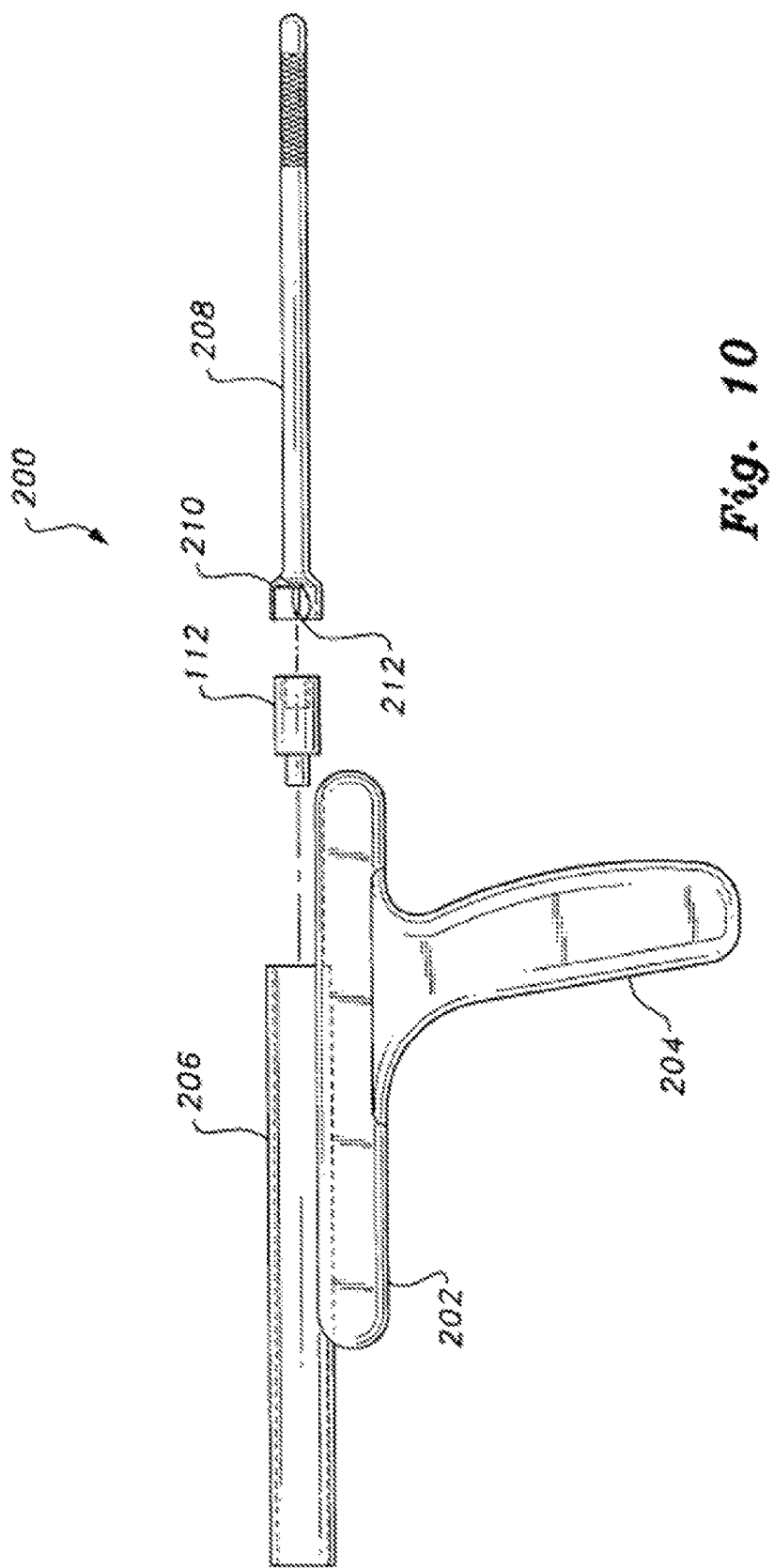
FIG. 10 is a side view of another alternative embodiment of the bioinjection device.

In the alternative embodiment of FIG. 10, device 200 allows for manual insertion and operation of the implant 112. A gripping handle portion 204 is secured to a lower surface of mount 202. Hollow insertion tube 206 is mounted on a front portion of the upper surface of mount 202, as shown. The rear portion of the upper surface of mount 202 may have a groove, ridge or other means for slidably holding implant 112. A plunger 208 is provided, with plunger 208 having a gripping, rear portion and a front portion terminating in a plunger head 210, with needle 212 being positioned centrally therein. In operation, the user loads an implant 112 onto the rear, upper surface of mount 202, as shown, and pushes implant 112 through tube 206, for insertion, with plunger head 210 pushing implant through tube 206 and needle 212 piercing the rear end of implant 112, as described above.

In another embodiment, a cartridge or tip of the bioinjection device is modified to include multiple dispensing apertures. In this way, directional control for dispersing the medicament (e.g., autograft, allograft, BMP), or any other substance, is enhanced.

Figure 11A:
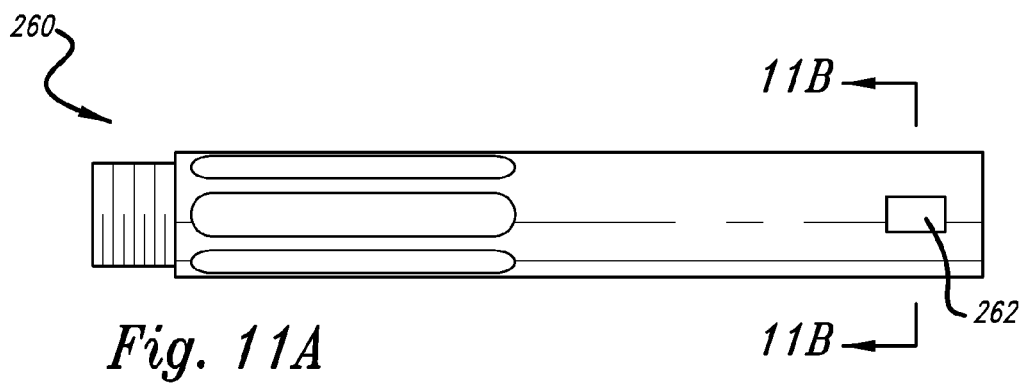
FIG. 11A is a side view of one embodiment of a tip or cartridge for use with a bioinjection device.
Figure 11B:
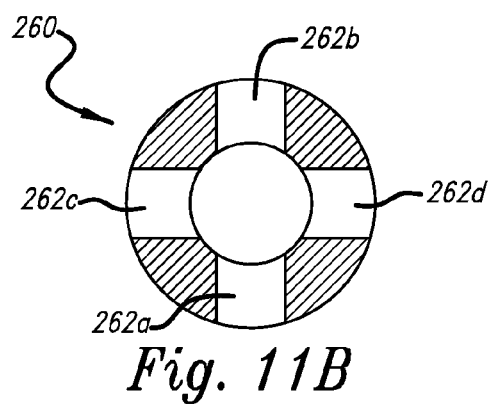
FIGS. 11B-11E are cross sectional views taken from line 11B-11B showing different arrangements of apertures in the tip or cartridge.
Figure 11C:
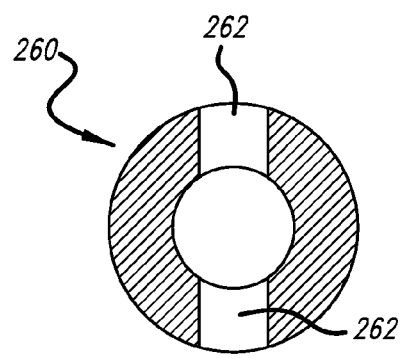
Figure 11D:
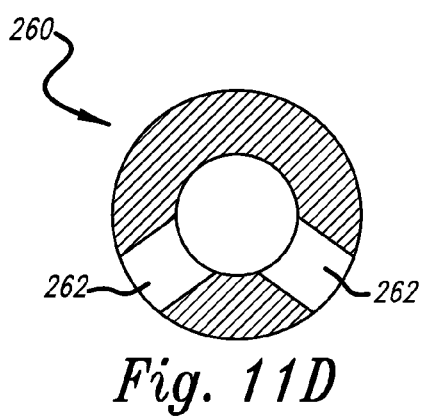
Figure 11E:
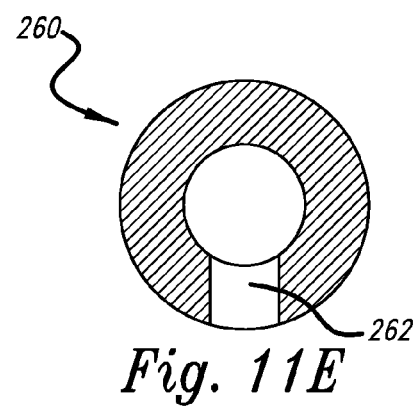

More particularly, as shown in FIGS. 11A and 11B, a tip 260 includes multiple openings or apertures 262 located distally. However, it will be appreciated that the location of such apertures 262 can be anywhere along the tip. For instance, the apertures 262 can be located along the tip equal-distant about the circumference of the tip as shown in the cross-sectional view of FIG. 11B. In FIG. 11B, the tip can include four openings, one located on the front side 262a of the tip, one located on the back side 262b of the tip, one located on the left side 262c of the tip and one located on the right side 262d of the tip. In another embodiment shown in FIG. 11C, two apertures 262 are located opposite each other along the circumference of the tip 260. In yet another embodiment, two or more apertures may be located any distance from each other along the circumference of the tip. Still further, two or more apertures 262 may be positioned on the same side of the tip 260 in a stacked configuration. One embodiment shown in FIG. 11D includes two apertures 262 located a certain distance around the circumference of the tip. The tip 260 may include a single aperture 262 as shown in FIG. 11E. Generally, the apertures 262 will have a diameter of 10 mm to 17 mm and a length of 5 mm; but any size diameter and/or length may be used.

Figure 12A:
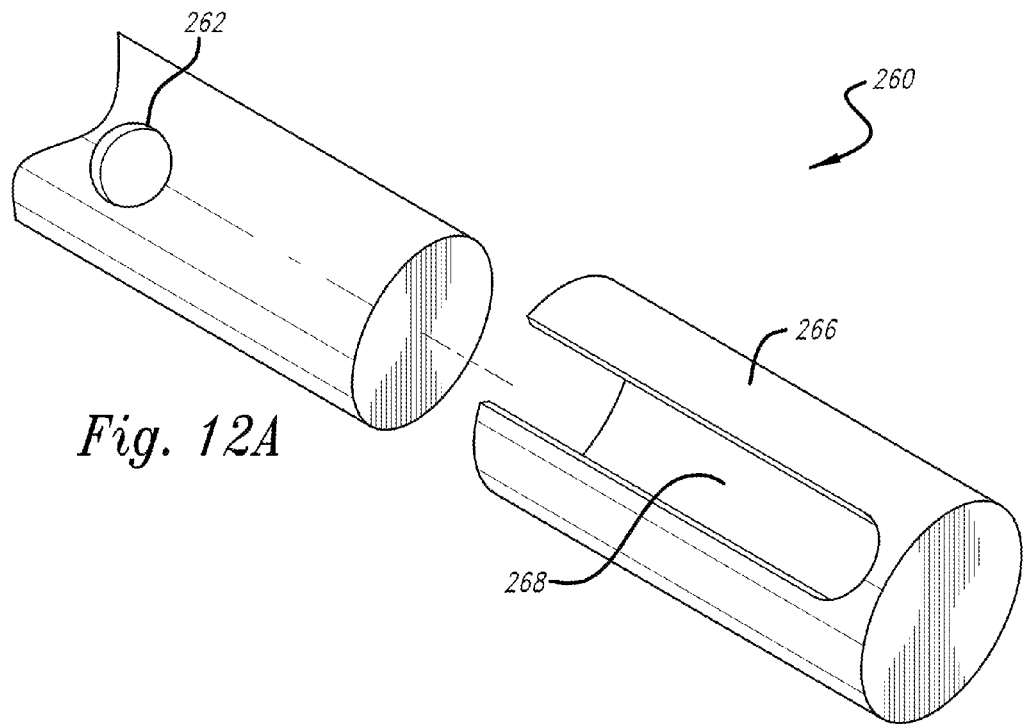
FIGS. 12A-12C show one embodiment of a tip or cartridge having a directional control member that can close, open, or partially open one or more apertures on the tip or cartridge.
Figure 13A:
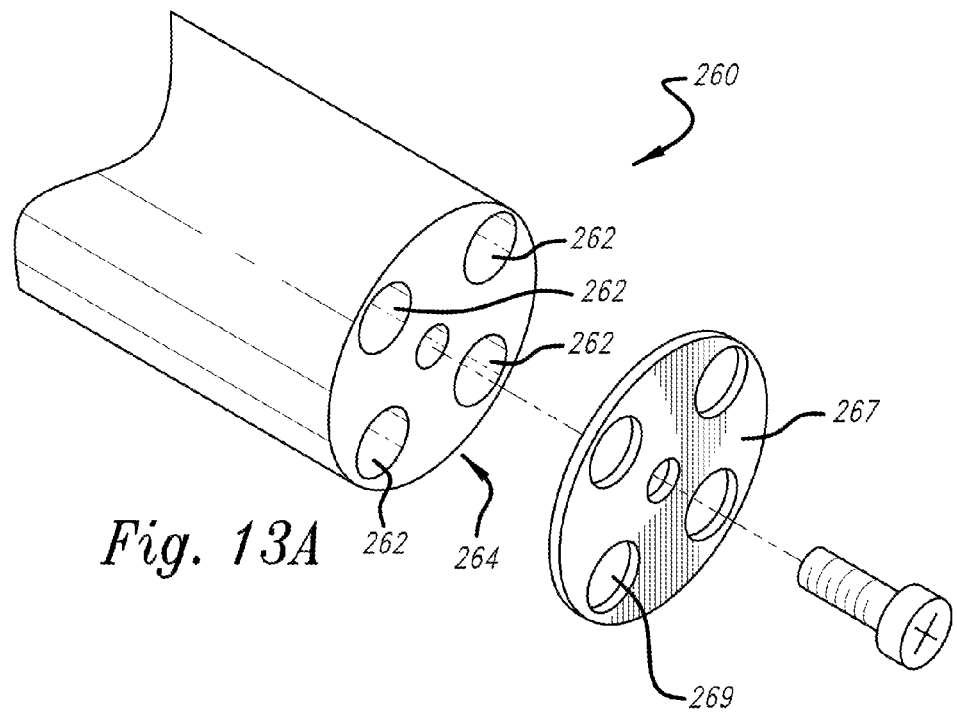
FIGS. 13A-13C show another embodiment of a tip or cartridge having a directional control member that can close, open, or partially open one or more apertures located on the distal end of the tip or cartridge.

It will be appreciated that any number of apertures, sizes, and locations on the tip may be used. For example, FIG. 12A depicts an aperture 262 disposed near the middle of the length of the body of the tip 260. As another example, FIG. 13A depicts apertures 262 formed on a distal end 264 of one embodiment of tip 260. In addition, the apertures 262 can take any shape such as, by way of example and not by limitation, oval, circular, square, rectangular, wavy, diamond and the like. Further, the apertures 262 can be the same shape or the apertures can each have a distinct shape from one or more other apertures.

Figure 12B:
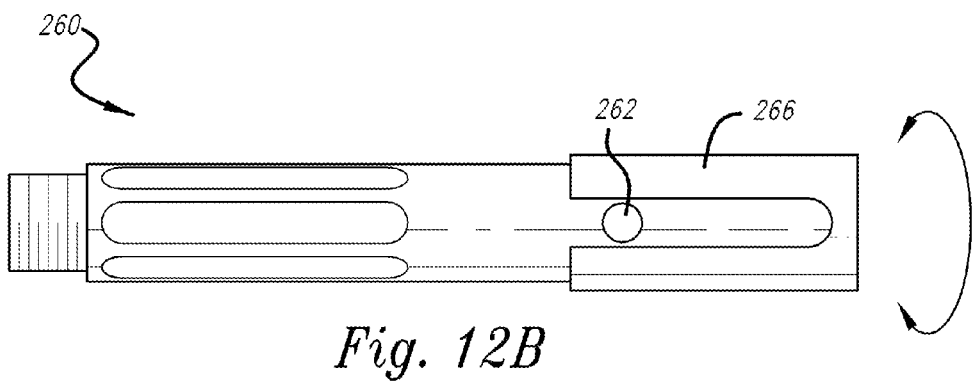
Figure 12C:
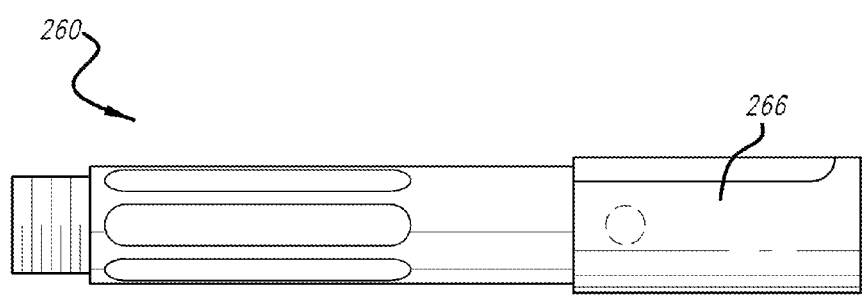

As shown in FIGS. 12A and 12B, included on the tip 260 may be a movable directional control member 266. This directional control member 266 is used to control dispersion of the medicament, or other substances, by covering and closing off one or more of the apertures 262 of the tip 260. This directional control member 266 may be made of any appropriate material, for instance, metal, polymers, acrylic, plastic, silicon, resins, or other substance. For example, by rotating the directional control member 266, the user can limit the dispersion of the medicament (and the amount thereof) towards a single direction to enhance dispersion of the medicament in that particular direction or angle within, by way of example only, a bone structure or other void as well as discs, cartilage and other body tissues. FIGS. 12A and 12B show the directional control member 266 having an opening or slot 268 over the aperture 262 so that medicament would be allowed to exit the selected aperture. In this embodiment, the directional control member 266 has only one opening or slot 268, but could have multiple openings or slots 268 to allow medicament to exit multiple openings at once. The size of the slot 268 may vary in order to allow more than one aperture to be open or to only allow a portion of one aperture to be open. It has also been contemplated that the directional control member 266 may have multiple slots positioned at any interval. FIG. 12C shows the directional control member 266 turned on the tip 260 such that the aperture 262 is blocked to prevent medicament from exiting the specific aperture 262. In one embodiment, an operator or user controls the directional control member by hand or otherwise manually moves the directional control member from a closed position to an open or partially open position.

Figure 13B:
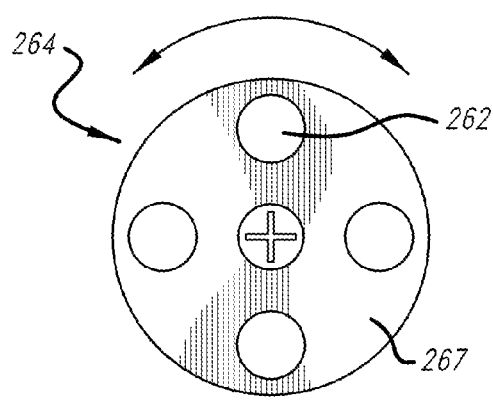
Figure 13C:
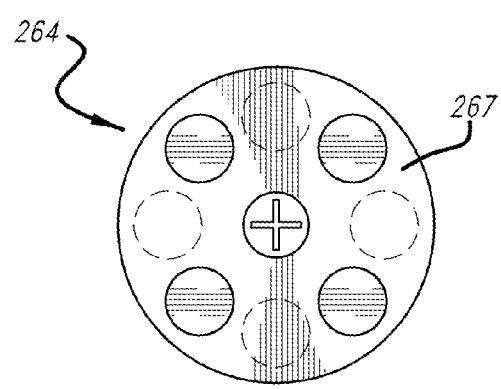

Another embodiment of a directional control member 267 having openings 269 can be configured to allow dispersion of the medicament, or other substances, in more than one direction to enhance the dispersion of the medicament and/or substances. For example, the medicament can be dispersed from multiple apertures 262 as shown in FIG. 13A. As shown in FIG. 13B, the operator can turn the directional control member 267 to close off all of the apertures 262. The directional control member 267 can be designed such that one or more selected apertures are opened or partially opened while other apertures remain closed. Again, this provides enhanced directional control over how and the amount of the medicament that the bioinjection device disperses from the tip 260.

Figure 14A:
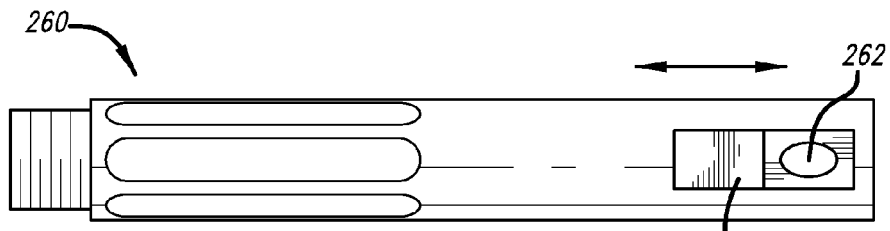
FIGS. 14A-14C are side views of another embodiment of a tip or cartridge having a sliding member that can close, open, or partially open one or more apertures on the tip or cartridge.
Figure 14B:
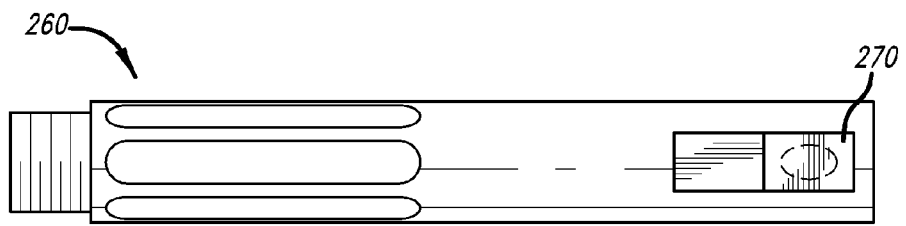
Figure 14C:
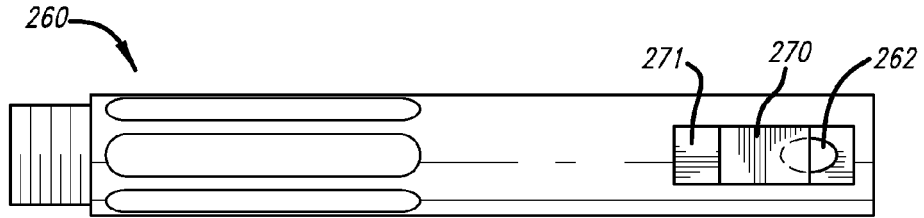

In still another embodiment, as shown in FIGS. 14A and 14B, each tip 260 includes a slidable member 270 that moves along a track 271 disposed on the body of the tip 260. The slidable member 270 slides over the apertures 262 into an open or a closed position. In addition, the slidable member 270 can selectively move to variably control the size of the opening or aperture 262 to further enhance the direction and amount of dispersion of the medicament. As shown in FIG. 14C, the slidable member 270 is positioned so that it covers only a portion of the aperture 262. It can be understood that the greater the size of the opening, the greater the dispersion amount. Still further, the user of the bioinjection device may operate the slidable member 270 and directional control members 266 and 267 manually and/or miniature motors or other mechanisms may control the slidable and/or rotatable members. In short, it will be appreciated that the tip 260 can be configured with any number of apertures 262, in any number or combinations of locations, with each of the apertures having the same or different sizes and/or shapes.

Figure 15A:
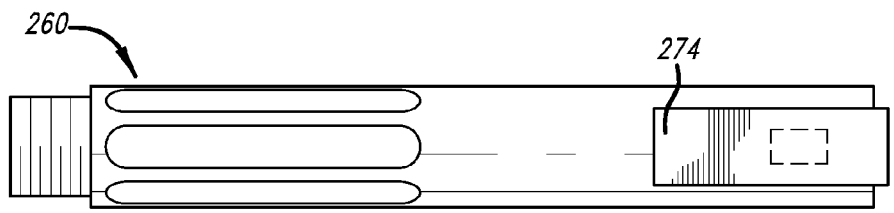
FIGS. 15A-15B are side views of yet another embodiment of a tip or cartridge with an aperture that is closed with a sealing member that can be removed.
Figure 15B:
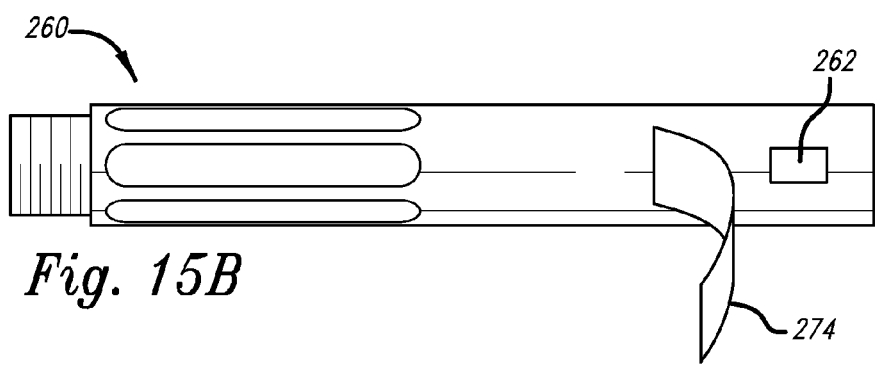

In another embodiment as shown in FIG. 15A, each aperture 262 of the tip 260 is initially sealed or closed to preclude any medicament from being dispensed therethrough. In this embodiment, one or more seals or sealing members 274, may be removed, perforated or otherwise opened as shown in FIG. 15B to allow the medicament to then be dispensed through the now open aperture(s) 262 while still precluding the dispensing of medicament from the remaining closed apertures. By way of example and not by way of limitation, the seals that initially close the apertures may be formed of foil, plastic, polymers, acrylics, thin metal strips, silicon or any other suitable material. For example, in one embodiment, a foil or plastic membrane may cover an aperture. This membrane may be completely removed by peeling it away from the tip and aperture. Alternatively, the membrane may be pierced to create multiple small openings or a single large opening therein to enable the medicament to be dispensed. In short, any combination of techniques may be used to initially seal the aperture and then to subsequently unseal the aperture for controlling the direction and/or angle of medicament dispersion.

In still another embodiment, interchangeable preformed tips 260 can be used with the bioinjecting device. In this embodiment, each tip forms a unitary, closed structure, except for the direction or directions in which the medicament is to be dispensed. For example, the tip 260 can have a single opening located anywhere along the circumference of the tip similar to the embodiment of the tip shown in FIG. 11E. Also, the tip 260 can have more than one opening therein to provide directional dispersion over a broader array of directions, such as the embodiments of tips shown in FIGS. 11B-11D. For example, tip openings or apertures 262 can be employed on the back side and the right side simultaneously or the back side and the left side simultaneously, or in any other combination of openings, to enhance the directional dispersion of the medicament. Again, the size, shape and orientation of the apertures can be uniform or vary amongst the apertures.

The tips 260 described above can be used with another embodiment of a bioinjection device 300. As shown in FIG. 16, device 300 is used to dispense medicament stored in the tip 260 into a fracture, degenerative tissue, or the like of a spinal segment. The medicament, which may be a bone morphologic protein, bone void filler, antibiotics, or the like, may be used for the healing of the spinal segment.

Bioinjection device 300 includes a housing 302 having a handle member 304 and a trigger member 306. The housing 302 also includes a grip 308 at a proximal end. An elongated tube 310 is mounted to the front (distal) end of housing 302, allowing for the dispensing of medicament from the tips 260 where immediate proximity of the surgeon's hands is not possible. The elongated tube 310 includes a proximal region 312 that is preferably solid and relatively non-flexible and is joined to a flexible portion 314 at the distal end thereof. The flexible portion 314 may be a coil or spring like structure. The flexible portion may assist the user in reaching certain areas of the body that require treatment. For example, if the treatment area is in the superior tibia, the flexibility of the distal end of the bioinjection device allows access beyond the supra patellar tendon. A head 316 of the elongated tube 310 is disposed distally to the flexible portion 314. In other embodiments, the head 316 is formed at the distal end of the flexible portion 314. Head 316 has an open outer end with internal threads formed therein. In this embodiment, the internal threads of the head 316 releasably attach to outer threads 317 formed on the tip 260. However, any means may be used to releasably attach the tip 260 to the bioinjection device 300, and further, the tip may be permanently attached to the bioinjection device.

An inner shaft 318 extends through tube 310 as best shown in FIG. 17. A front or distal end of the inner shaft 318 may include a blunt end 320. The shaft 318 may instead include a rounded or pointed end. The rear or proximal end of the inner shaft 318 is in connection with the trigger member 306. In one embodiment, the proximal end of the inner shaft 318 is secured to a lever arm that is connected to the trigger member 306, similar to the structure shown in FIG. 2. Thus, rotation of trigger member 306 with respect to the handle member 304 drives forward sliding translation of the inner shaft 318 with respect to the elongated tube 310; i.e., actuation of trigger member 306 causes forward sliding of inner shaft 318 within the elongated tube 310.

When the trigger member 306 is not actuated, the blunt end 320 of the inner shaft 318 is positioned within the opening of the head 316. Once the trigger member 306 is actuated and the inner shaft 318 slides forward, the blunt end 320 of the inner shaft moves forward or distal to the head 316 and enters the cavity of the tip 260. As the blunt end 320 continues to move forward, it engages and pushes a plunger 322 located within the tip 260. Pushing the plunger 322 of the tip 260 distally forces medicament 324 stored within the tip 260 through the open aperture(s) 262.

It will also be appreciated that the medicament contained within the cartridges or tips 260 can be prepared and loaded either at a remote facility or locally within the sterile field of an operating room or any other procedure room or environment. When prepared locally, the physician or someone under his control and direction may prepare the medicament cartridges or tips to meet the specific needs for the patient at the time of surgery or other procedures. This greatly enhances the flexibility and efficacy of this technology. Still further, it will be understood that persons other than physicians, including nurses, physician assistants or any other person required or needing to use the bioinjection device, may use the bioinjection device.

Furthermore, the various embodiments described above are provided by way of illustration only and should not be construed to limit the invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A bioinjection device, comprising:
a housing having a handle member and an elongated barrel connected to the handle member, the elongated barrel having a channel and a distal end defining an opening;
a trigger pivotally mounted on the housing;
an inner shaft having an end portion, the inner shaft is received within the elongated barrel, the inner shaft being slidable along the channel of the elongated barrel between a first position in which the end portion of the inner shaft is retracted within the elongated barrel and a second position in which the end portion of the inner shaft extends past the opening at the distal end of the elongated barrel;
a tip positioned at the most distal end of the bioinjection device, the entire tip removably attachable to the distal end of the elongated barrel, the tip containing a medicament, the medicament being disposed in the most distal portion of the tip before use of the bioinjection device, and the tip including a plurality of apertures for dispensing the medicament; and
a spring-loaded actuation mechanism coupling the trigger with the inner shaft to force the medicament contained in the tip through the plurality of apertures of the tip into a body tissue positioned adjacent to the tip when the trigger is actuated.

2. The bioinjection device of claim 1, further comprising a directional control member that is operative to selectively control the amount of dispersion of medicament from each of the plurality of apertures.

3. The bioinjection device of claim 2, wherein the directional control member is rotatable to close at least one aperture of the plurality of apertures while leaving at least another one aperture of the plurality of apertures in an open position for dispensing the medicament.

4. The bioinjection device of claim 2, wherein the directional control member is used to control the location or angle of dispersion of the medicament.

5. The bioinjection device of claim 1, wherein the plurality of apertures are located along the tip equal-distant about the circumference of the tip.

6. The bioinjection device of claim 1, wherein the plurality of apertures has a diameter between 10 millimeters and 17 millimeters.

7. The bioinjection device of claim 1, wherein the plurality of apertures is 5 millimeters in length.

8. The bioinjection device of claim 1, wherein the medicament can be prepared to a desired specification during a procedure.

9. The bioinjection device of claim 1, wherein the medicament is comprised of one or more from the group comprising autograft, allograft and BMP.

10. A bioinjection device, comprising:
a housing having a handle member and an elongated barrel connected to the handle member, the elongated barrel having a channel and a distal front end defining an opening;
a trigger pivotally mounted on the housing;
an inner shaft having an end portion received within the channel of the elongated barrel, the inner shaft being slidable between a first position in which the end portion of the inner shaft is retracted within the elongated barrel and a second position in which the end portion of the inner shaft extends past the opening at the distal front end of the elongated barrel;
a tip positioned at the most distal end of the bioinjection device, the entire tip removably attachable to the distal front end of the elongated barrel, the tip containing a medicament, the medicament being disposed in the most distal portion of the tip before use of the bioinjection device, and the tip having a plurality of apertures for enabling dispensing of the medicament therethrough and into a body tissue positioned adjacent to the tip when the inner shaft is in the second position; and
the plurality of apertures each having an initial sealed state so that one of more of the plurality of apertures can subsequently be opened by a user of the bioinjection device to control the direction of dispersion of the medicament through the one or more of the plurality of apertures.

11. The bioinjection device of claim 10, wherein the plurality of apertures have a diameter between 10 millimeters and 17 millimeters.

12. The bioinjection device of claim 10, wherein the plurality of apertures are 5 millimeters in length.

13. The bioinjection device of claim 10, wherein the plurality of apertures are located along the tip equal-distant about the circumference of the tip.

14. The bioinjection device of claim 10, wherein each of the plurality of apertures are sealed using one or more materials in the group comprising foil, plastic, silicon, polymers, acrylics, and metal strips.

15. The bioinjection device of claim 10, wherein each of the plurality of apertures may be selectively opened, perforated, or removed to control the direction or angle of medicament dispersion.

16. The bioinjection device of claim 10, wherein the medicament includes of one or more from the group comprising autograft, allograft and BMP.

17. The bioinjection device of claim 10, wherein the plurality of apertures vary in size, one from the other.

18. The bioinjection device of claim 10, wherein the plurality of apertures vary in shape, one from the other.

19. The bioinjection device of claim 10, wherein the plurality of apertures are all of the same shape.

* * * * *

UNITED STATES PATENT AND TRADEMARK OFFICE
CERTIFICATE OF CORRECTION

PATENT NO. : 9,750,879 B2
APPLICATION NO. : 14/060484
DATED : September 5, 2017
INVENTOR(S) : Clifford T. Solomon et al.

Page 1 of 1

It is certified that error appears in the above-identified patent and that said Letters Patent is hereby corrected as shown below:

In the Claims

Column 12, Line 63: Claim 10:
"state so that one of more of the plurality of apertures" should read, --state so that one or more of the plurality of apertures--.

Column 13, Line 18: Claim 16:
"medicament includes of one or more from the group" should read, --medicament includes one or more from the group--.

Signed and Sealed this
Twenty-fourth Day of April, 2018

Andrei Iancu
*Director of the United States Patent and Trademark Office*